(12) United States Patent
Glickman et al.

(10) Patent No.: US 10,188,827 B2
(45) Date of Patent: Jan. 29, 2019

(54) DISTAL CLOSING CATHETERS AND METHODS FOR SAME

(71) Applicant: UROPHARMA LIMITED, Norwich, Norfolk (GB)

(72) Inventors: Scott Glickman, Aylesbury (GB); Howard Shapland, Bungay (GB)

(73) Assignee: Uropharma Limited, Mountergate, Norwich (GB)

( * ) Notice: Subject to any disclaimer, the term of this patent is extended or adjusted under 35 U.S.C. 154(b) by 0 days.

(21) Appl. No.: 14/351,936

(22) PCT Filed: Oct. 22, 2012

(86) PCT No.: PCT/GB2012/052617
§ 371 (c)(1),
(2) Date: Apr. 15, 2014

(87) PCT Pub. No.: WO2013/057517
PCT Pub. Date: Apr. 25, 2013

(65) Prior Publication Data
US 2015/0290421 A1 Oct. 15, 2015

(30) Foreign Application Priority Data
Oct. 20, 2011 (GB) .................. 1118126.0

(51) Int. Cl.
*A61M 25/00* (2006.01)
*A61M 25/10* (2013.01)
*A61M 25/01* (2006.01)

(52) U.S. Cl.
CPC ........ *A61M 25/003* (2013.01); *A61M 25/007* (2013.01); *A61M 25/0075* (2013.01);
(Continued)

(58) Field of Classification Search
CPC .............. A61M 25/003; A61M 25/007; A61M 25/0075; A61M 25/10; A61M 25/0026;
(Continued)

(56) References Cited

U.S. PATENT DOCUMENTS

| 4,834,702 A | 5/1989 | Rocco |
| 6,132,364 A | 10/2000 | Rottenberg et al. |

(Continued)

FOREIGN PATENT DOCUMENTS

| CN | 1145260 A | 3/1997 |
| DE | 101 12 630 | 7/2002 |

(Continued)

OTHER PUBLICATIONS

GB Application No. 1118126.0 Search Report dated Jan. 23, 2012 (2 pages).
(Continued)

*Primary Examiner* — Kami A Bosworth
*Assistant Examiner* — Leah Swanson
(74) *Attorney, Agent, or Firm* — Schwegman Lundberg & Woessner, P.A.

(57) ABSTRACT

A catheter for insertion into a body cavity of a subject (such as the urinary bladder), and having a drainage tube extending from a drainage opening adjacent a distal end of the catheter to a drainage outlet adjacent a proximal end of the catheter; a closure member mountable for sliding movement within the drainage tube between a first position such that said drainage opening is in fluid communication with the drainage outlet and a second position wherein the closure member blocks fluid communication between the drainage opening and the outlet port; and an actuator, operable from the proximal end of the catheter, to move the closure member between the first and second positions. The closure (Continued)

member can include a second tube, sliding within the drainage tube, or a slideable plug.

19 Claims, 6 Drawing Sheets

(52) U.S. Cl.
CPC ......... *A61M 25/10* (2013.01); *A61M 25/0026* (2013.01); *A61M 25/01* (2013.01); *A61M 2025/0018* (2013.01); *A61M 2025/0031* (2013.01); *A61M 2025/0175* (2013.01)

(58) Field of Classification Search
CPC .. A61M 2025/0018; A61M 2025/0031; A61M 2025/0175; A61M 25/0017; A61M 2210/1078; A61M 2210/1085; A61M 2210/1089; A61M 2210/1092; A61M 2210/1096; A61F 2/045; A61F 2002/047; A61F 2002/048
USPC .................................................. 604/31, 544
See application file for complete search history.

(56) References Cited

U.S. PATENT DOCUMENTS

| | | | |
|---|---|---|---|
| 6,270,053 B1* | 8/2001 | Eshel | A61F 5/4405 |
| | | | 251/4 |
| 8,007,488 B2 | 8/2011 | Ravenscroft | |
| 2005/0038413 A1* | 2/2005 | Sansoucy | A61M 25/003 |
| | | | 604/537 |
| 2005/0124969 A1 | 6/2005 | Fitzgerald et al. | |
| 2006/0184224 A1* | 8/2006 | Angel | A61F 2/95 |
| | | | 623/1.11 |
| 2007/0213671 A1 | 9/2007 | Hiatt | |
| 2007/0232981 A1* | 10/2007 | Ravenscroft | A61M 25/003 |
| | | | 604/6.16 |
| 2008/0091166 A1 | 4/2008 | Fitzgerald et al. | |
| 2008/0228258 A1 | 9/2008 | Gerdts et al. | |
| 2008/0287888 A1 | 11/2008 | Ravenscroft | |
| 2008/0312578 A1* | 12/2008 | DeFonzo | A61M 25/003 |
| | | | 604/6.16 |
| 2009/0240234 A1* | 9/2009 | Doerr | A61M 25/10 |
| | | | 604/517 |
| 2009/0264860 A1 | 10/2009 | Hiatt | |
| 2010/0204771 A1* | 8/2010 | Olson | A61F 2/856 |
| | | | 623/1.11 |
| 2012/0053564 A1 | 3/2012 | Ravenscroft | |
| 2012/0168324 A1 | 7/2012 | Carleo | |
| 2012/0179144 A1 | 7/2012 | Carleo | |
| 2012/0239006 A1* | 9/2012 | Wijay | A61M 25/0017 |
| | | | 604/544 |

FOREIGN PATENT DOCUMENTS

| | | | | |
|---|---|---|---|---|
| DE | 10112630 C2 | 3/2003 | | |
| EP | 0 245 211 | 11/1987 | | |
| GB | 2448892 A | 11/2008 | | |
| GB | 2484598 | 2/2014 | | |
| JP | 09253215 A | 9/1997 | | |
| JP | 2001137350 | 5/2001 | | |
| JP | 2002510536 A | 4/2002 | | |
| WO | WO 2007/079152 | 7/2007 | | |
| WO | WO 2008/097949 | 8/2008 | | |
| WO | WO 2008132431 A1 * | 11/2008 | ........ A61M 25/0017 |
| WO | WO 2010/014569 | 2/2010 | | |
| WO | WO 2011/019359 | 2/2011 | | |
| WO | WO 2011/014201 | 3/2011 | | |
| WO | WO-2011045790 A1 | 4/2011 | | |
| WO | WO-2013057517 | 4/2013 | | |

OTHER PUBLICATIONS

PCT/GB2012/052617 International Search Report dated Jan. 1, 2013 (3 pages).
International Application Serial No. PCT/GB2012/052617, International Preliminary Report on Patentability dated Feb. 5, 2014, 5 pgs.
International Application Serial No. PCT/GB2012/052617, Written Opinion dated Jan. 21, 2013, 5 pgs.
A United Kingdom Application Serial No. 1118126.0, Office Action dated Jul. 26, 2013, 2 pgs.
U.S. Appl. No. 15/962,227, Preliminary Amendment filed Apr. 26, 2018, 8 pgs.

* cited by examiner

DISTAL CLOSING CATHETERS AND METHODS FOR SAME

This application claims priority to International Application No. PCT/GB2012/052617 filed Oct. 22, 2012 and GB Appln. No. 1118126.0 filed Oct. 20, 2011; the entire contents of each are incorporated herein by reference.

FIELD OF THE INVENTION

The invention relates to catheters for draining fluids from body cavities of human or animal subjects and especially for those catheters that can also instill a medicament into the cavity following drainage. The invention is especially concerned with such catheters for draining urine from the urinary bladder of a subject and instilling a medicament therein.

BACKGROUND AND PRIOR ART KNOWN TO THE APPLICANT

There are a number of conditions that require patients to manually drain urine from the bladder at intervals, and this can be performed either under the supervision of an attending physician or healthcare worker, or on occasions can be performed by a patient themselves. One such common condition is an overactive bladder. For many conditions it is also necessary to deliver a medicament to the bladder. For this to be successful, it is important that the bladder is initially drained of any accumulated urine to prevent dilution of the medicament, so allowing a pre-determined dose to be applied. Direct application of medicaments to the interior of the bladder, known as "intravesical" administration is becoming more common, and one such specialized catheter to allow drainage and intravesical administration is described in UK patent GB 2448892. In this device, a urinary cannula is described, and that comprises a number of channels extending from a proximal to a distal end of the catheter. There is a drainage channel to allow urine to flow from one end to the other; and an instillation channel to allow medicament to be delivered from the proximal to the distal end and a control channel to allow a viscous control fluid to be delivered to a cuff located within the drainage channel. In some embodiments a further channel is provided to allow delivery of a fluid to a balloon adjacent to the external wall of the catheter, known as a Foley balloon, which may be inflated to secure the end of the catheter at the correct position in the bladder after insertion via the urethra.

Such devices are complex and expensive to manufacture, and it is an object of the present invention to provide an improved such catheter.

SUMMARY OF THE INVENTION

Accordingly, the invention provides a catheter for insertion into a body cavity of a subject, comprising: a drainage tube extending from a drainage opening adjacent a distal end of the catheter to a drainage outlet adjacent a proximal end of the catheter; a closure member mountable for sliding movement within said drainage tube between a first position such that said drainage opening is in fluid communication with said drainage outlet and a second position wherein said closure member blocks fluid communication between said drainage opening and said outlet port; and an actuator, operable from the proximal end of the catheter, to move said closure member between said first and second positions. In this way, a simplified device is provided, having a slideable closure member, rather than an internally-mounted inflatable balloon as previously provided on such catheters. This simplifies manufacture, and also simplifies operation, as the valve closure mechanism is less likely to be confused with the other ports often seen on such catheters. This is especially important if the device is to be used by the patient themselves.

Preferably, the catheter further comprises an instillation lumen extending from an instillation port adjacent a proximal end of the catheter to an instillation outlet adjacent a distal end of the catheter. More preferably, the catheter further comprises a non-return valve 200 configured to resist flow in said instillation lumen in a direction from the distal end to the proximal end.

In preferable embodiments, said actuator is configured to move said closure member between said first and second positions irreversibly. In this way, re-use of the device is prevented, thereby reducing the risk of cross-infection.

In a first preferable variant, said closure member comprises a plug and said actuator comprises a filament attached to said plug, said filament extending to the proximal end of the catheter.

In a second preferable variant, said closure member comprises a secondary tube located within said drainage tube, said secondary tube having an aperture in its wall such that, in said first position said aperture fluidly communicates with said drainage opening and in said second position said fluid communication is blocked, and wherein said secondary tube extends to the proximal end of said catheter such that it may be manipulated to slideably move said tube between its first and second positions, thereby acting as said actuator.

Preferably, the second variant is configured such that said sliding movement is in an axial direction. More preferably, the cross-sectional profile of said drainage tube and the profile of the outside surface of said secondary tube are so shaped as to resist relative rotational movement therebetween whilst allowing relative axial movement therebetween.

In an alternative arrangement, the second variant is configured such that said sliding movement comprises rotation of said secondary tube relative to said drainage tube. Preferably, a cooperating indent and detent are provided on the outside surface of said secondary tube and the internal wall of said drainage tube configured to allow relative rotational movement between the secondary tube and the drainage tube whilst resisting relative axial movement therebetween.

In any aspect or variant of the invention it is preferred that a lubricating agent is provided between said closure member and the internal wall of said drainage tube to facilitate relative movement therebetween and/or to provide a fluid resistant seal therebetween.

In any aspect of the second variant, it is preferred that a ratchet mechanism is provided to ensure irreversible movement of the secondary tube relative to the drainage tube.

In any aspect of either variant, it is also preferred that the catheter further comprises a balloon adjacent an external wall of the catheter near its distal end and proximal of said drainage opening and connected through a balloon control channel to a balloon control port at the proximal end, the balloon being inflatable and deflatable to respectively increase and decrease the local diameter of the catheter to allow reversible anchoring of the catheter within a body cavity.

DESCRIPTION OF PREFERRED EMBODIMENTS

Figure 1:
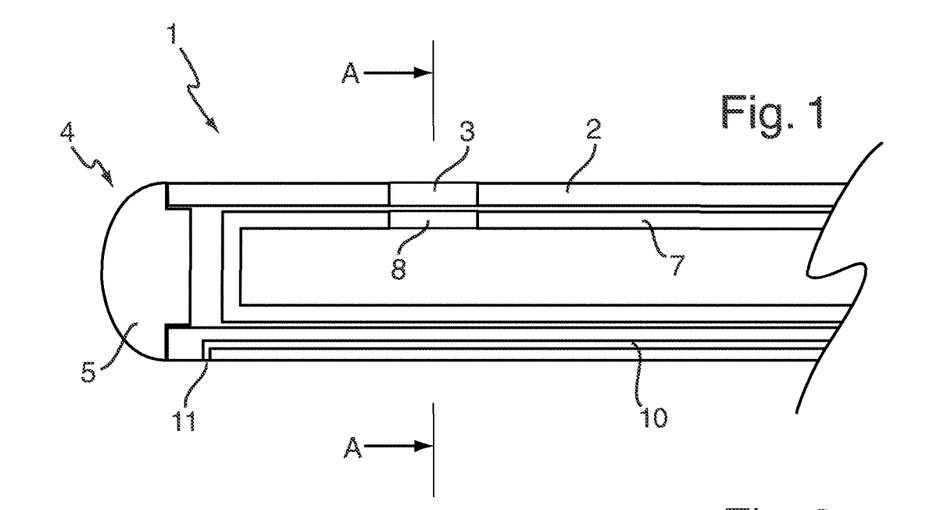
FIGS. 1 and 2 illustrate an axial cross-section of the distal end of a catheter of the present invention.

FIG. 1 illustrates, in axial cross-sectional view, the distal end of a catheter of the present invention, generally indicated by 1. In this embodiment, there is provided a drainage tube 2 that extends from a drainage opening 3 adjacent the distal end 4 of the catheter to a drainage outlet adjacent a proximal end of the catheter (not illustrated). The drainage tube 2 is constructed of a flexible material, such as a silicone-based plastics material or latex. The diameter of the catheter is so sized as to be able to be introduced into a body cavity of a subject for example through a urethra. In the embodiment of FIG. 1 the drainage tube 2 is sealed at its distal end by a cap 5 securely fitted to the end of the tube 2.

A closure member in the form of a secondary tube 7 located within the drainage tube 2. The bore of the drainage tube 2 and the outside diameter of the secondary tube 7 are so sized as to provide a relatively snug fit, whilst allowing the secondary tube 7 to slide within the drainage tube 2 along its full length. In this embodiment, the secondary tube 7 is provided with an aperture 8 in its wall that, in a first position as illustrated in FIG. 1, fluidly communicates with the drainage opening 3 in the drainage tube and thus with the lumen of the secondary tube 7.

Figure 2:
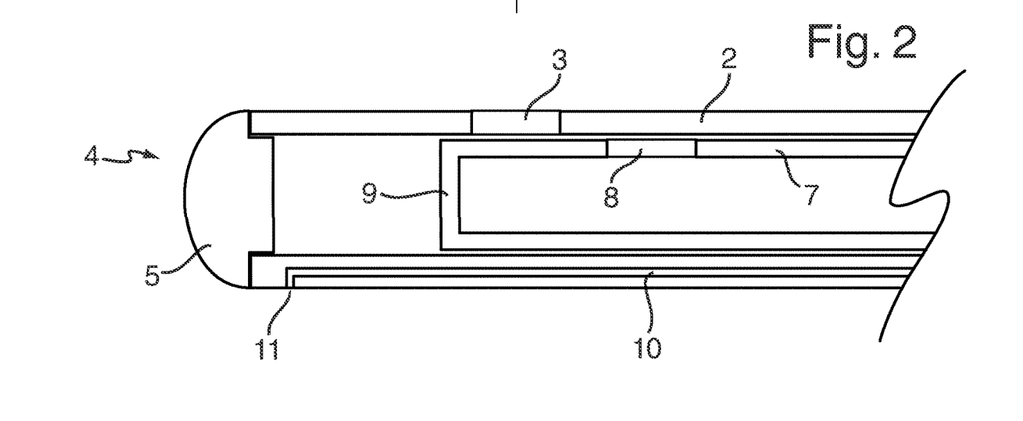

The secondary tube 7 may be slid within the drainage tube to a second position, illustrated in FIG. 2, such that the aperture 8 is no longer in fluid communication with the drainage opening 3 thereby blocking flow of a fluid through the drainage opening 3 and down the drainage tube or secondary tube. In the embodiment shown in FIGS. 1 and 2, the end of the secondary tube 7 is also sealed, for example with a cap or a plug 9. In this way, if the end of the secondary tube 7 is withdrawn to a distance past the drainage opening 3 towards the proximal end of the catheter, fluid can still not flow through the drainage tube and down the secondary tube.

Also included in this embodiment is an instillation lumen 10, located within the wall of the drainage tube 2 that extends from an instillation outlet 11 adjacent the distal end 4 of the catheter to an instillation port adjacent the proximal end of the catheter (not illustrated).

Figure 3:
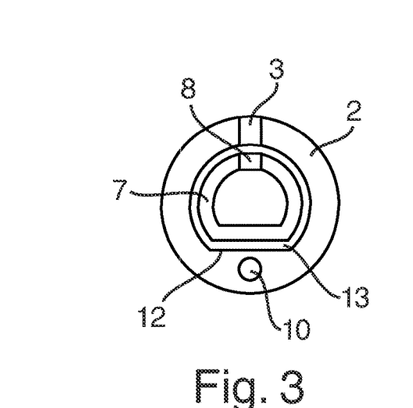
FIG. 3 illustrates a transverse cross-section of a catheter of the invention.

FIG. 3 shows a particularly preferred configuration of this embodiment, as a transverse cross-section along the line A-A of FIG. 1. In this embodiment, the bore of the drainage tube 2 is provided with a shaped profile, in the form of a flat section 12 running the length of the drainage tube, and the outside surface of the secondary tube 7 is provided with a similarly shaped flat surface portion 13 that co-operates with the flat 12 to resist rotational movement of the secondary tube with respect to the drainage tube. In this way, the configuration ensures that the aperture 8 in the secondary tube can be correctly aligned with the drainage opening 3.

It will be appreciated that in embodiments of the catheter, multiple drainage openings 3 may be provided around the periphery of the drainage tube, for example two such outlets, to ensure that flow can be maintained even if one outlet becomes blocked. It will be understood that in this situation, corresponding multiple apertures 8 in the secondary tube will also be provided.

Figure 4:
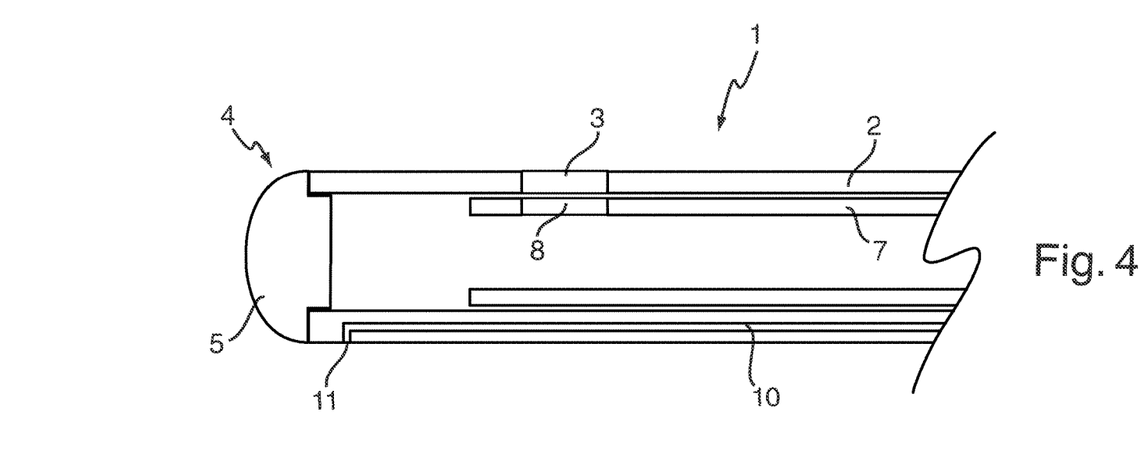
FIGS. 4 and 5 illustrate transverse cross-sections of the distal end of a catheter of the invention.
Figure 5:
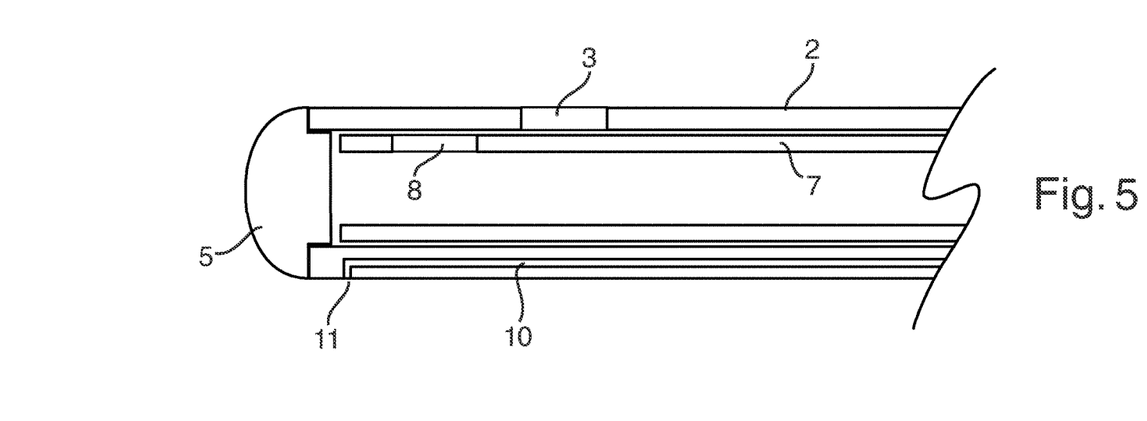

FIGS. 4 and 5 illustrate alternative configurations of the distal end of a catheter 1 of the present invention again in axial cross-section. Features in these embodiments that correspond with those of FIGS. 1 and 2 are numbered accordingly. The key difference between this embodiment and the embodiment of FIGS. 1 and 2 is that the secondary tube 7 is not provided with an end cap 9. It can be seen that if the drainage tube 2 and secondary tube 7 are arranged in such a way that the secondary tube 7 can only be moved from its first position (illustrated in FIG. 4) to a second position (illustrated in FIG. 5) by moving the secondary tube 7 towards the distal end 4 of the catheter, then such a cap on the secondary tube becomes unnecessary, as the wall of the secondary tube will always provide an adequate seal for the drainage opening 3.

Figure 6:
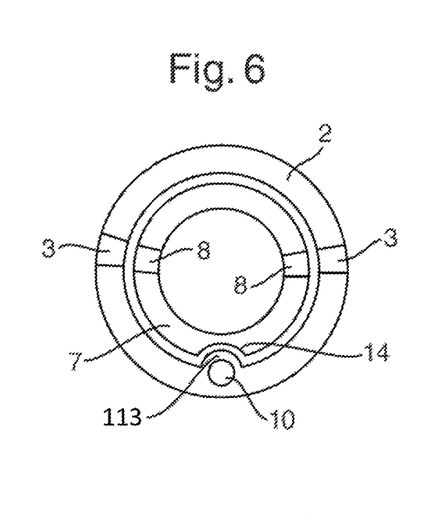
FIGS. 6-8 illustrate transverse cross-sections of embodiments of a catheter of the invention.

FIG. 6 illustrates an alternative configuration of a cross-section of a catheter of the present invention taken at a position equivalent to A-A of FIG. 1 and in which two drainage openings 3 are provided, together with two apertures 8 in the wall of a secondary tube 7. Again, an instillation lumen 10 is provided, molded into the wall of the drainage tube 2. In this embodiment, the instillation lumen defines a protuberance 113 in the inner wall of the drainage tube 2 that matches a longitudinal groove 14 along the outside wall of the secondary tube 7. These correspondingly-shaped profiles again provide a resistance against relative rotational movement between the drainage tube and the secondary tube, ensuring axial alignment of the apertures 8 with the drainage openings 3.

Figure 7:
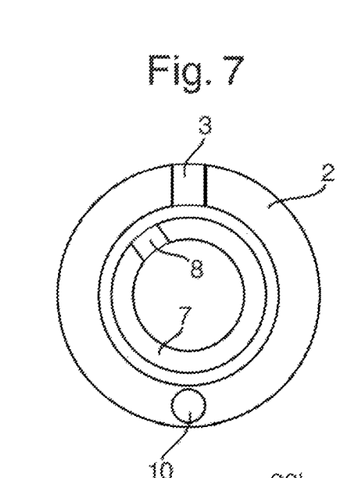

FIG. 7 illustrates an alternative cross-section, again at a position corresponding to section A-A of FIG. 1 in which the sliding movement of the secondary tube 7 relative to the drainage tube 2 is a relative rotational movement such that the drainage opening 3 may be aligned or, as illustrated, set out of alignment with the aperture 8 in the wall of the secondary tube 7.

Figure 8:
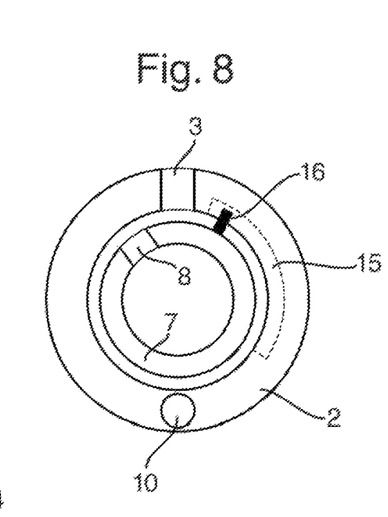

FIG. 8 illustrates a preferred variant of the feature illustrated in FIG. 7, wherein a corresponding indent 15 and detent 16 are provided on the outside surface of the secondary tube 7 and the internal wall of the drainage tube 2 to allow rotational movement between the secondary tube 7 and the drainage tube 2, but to resist relative axial movement there between. Again, such a configuration allows the drainage outlet 3 and aperture 8 to be reliably positioned either in or out of alignment.

It will be appreciated that such a detent and indent mechanism could be arranged to provide a combination of rotational and axial movement by, for example, providing a helically disposed indent 15 that co-operates with a protruding detent 16.

Figure 9:
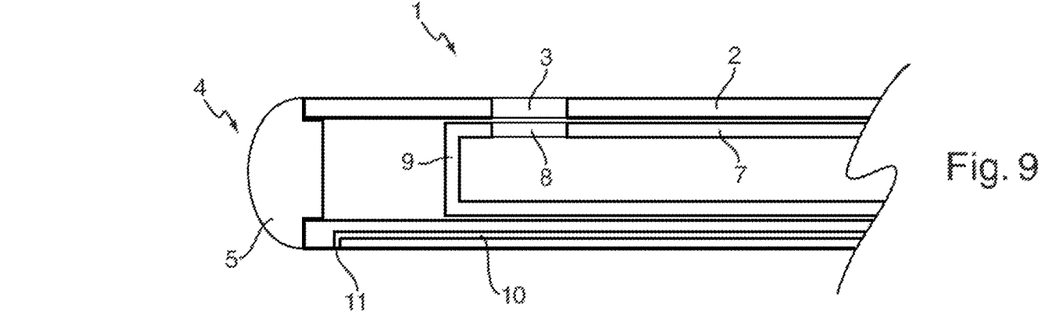
FIGS. 9 and 10 illustrate axial cross-sections of a distal and proximal end respectively of an embodiment of the invention.
Figure 10:
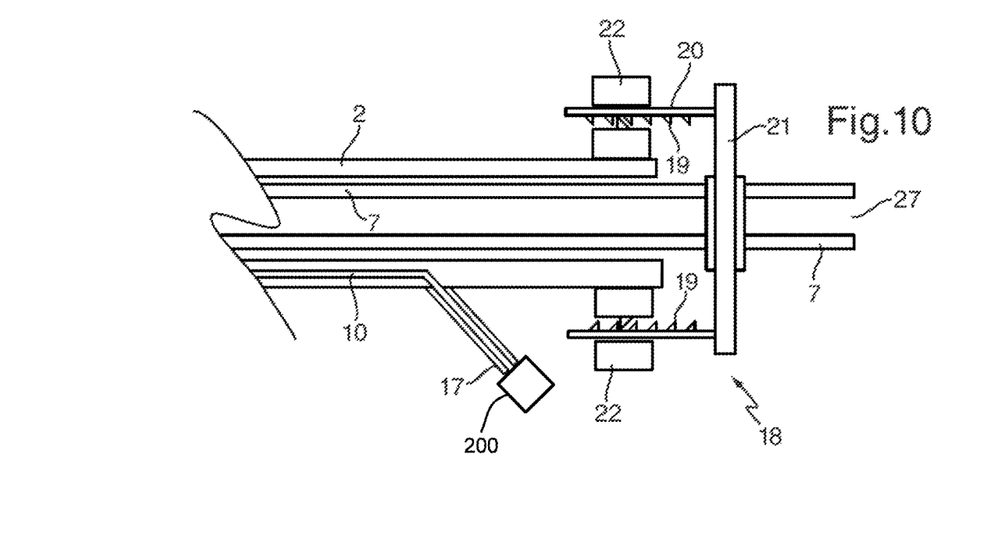

FIG. 9 and FIG. 10 illustrate respectively the distal and proximal ends of a catheter of the present invention. The intervening length of catheter is not illustrated, for clarity, but would typically have a length of between for example 30 cm to 1 m. Features common to those illustrated in earlier embodiments are correspondingly numbered. At the distal end of the catheter 1 illustrated in FIG. 9, the end of the secondary tube 7 is illustrated as being sealed with a plug 9, but could be equally open, as illustrated in the embodiments of FIGS. 3 and 4 due to the arrangement at the proximal end, to be described.

FIG. 10 illustrates the proximal end of the catheter 1 showing the exit of the instillation lumen 10 to an instillation port 17 adjacent the proximal end of the catheter. In this illustration, the port 17 is shown merely as the end of a tube, but could preferably and conveniently be provided with an appropriate connector such as a Luer connector, or in particularly preferred embodiments a self-sealing septum and/or a one-way valve (not illustrated).

FIG. 10 illustrates that in this embodiment the secondary tube 7 is connected to the drainage tube 2 by means of a ratchet mechanism, generally indicated by 18. The ratchet mechanism 18 has co-operating barbs 19 attached to elongate members 20 and connected to the secondary tube 7 via a pressure plate 21 connected to the outside of the secondary tube 7. The drainage tube 2 is connected to the receiving portion 22 of the ratchet mechanism 18. In use, the pressure plate 21 of the mechanism can be pushed toward the distal end of the catheter thereby moving the secondary tube 7 slidably within the drainage tube 2 and moving the tubes from the configuration shown in FIG. 9 to that illustrated in FIG. 5, thereby closing the flow path between the distal and proximal ends of the catheter through the lumen of the secondary tube 7. The ratchet mechanism 18 prevents the catheter being returned to its flow configuration, thereby preventing re-use of the device and hence preventing cross-infection that might result from re-use of the device.

Figure 11:
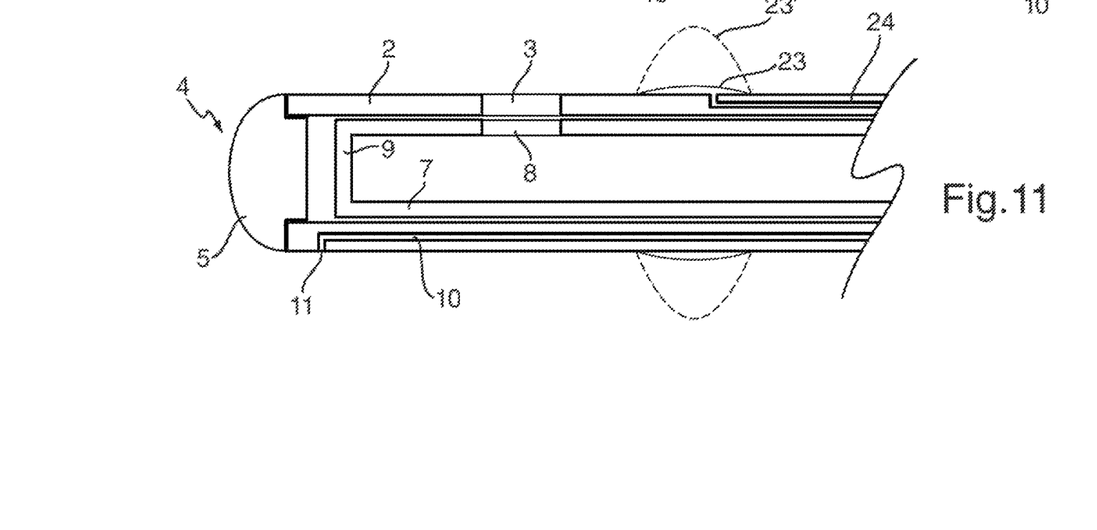
FIGS. 11-13 illustrate axial cross-sections of a distal end of a catheter of the present invention.

FIG. 11 illustrates in axial cross-sectional view, the distal end of a further embodiment of a catheter of the present invention. Again, features corresponding to those illustrated in other figures are numbered accordingly. In this embodiment, the catheter is further provided with a balloon 23 and 23' adjacent an external wall of the drainage tube 2 near the distal end 4 of the catheter but proximal of the drainage opening 3 and preferably the instillation opening 11. The interior of the balloon 23 is connected through a balloon control channel 24 to a balloon control port at the proximal end of the catheter (not illustrated) allowing the balloon to be inflated from a first position 23 to an inflated position 23' to anchor the catheter within the body cavity, for example at the neck of the urinary bladder. The balloon may subsequently be deflated to allow the catheter to be removed once drainage and/or instillation of medicament have been carried out.

Figure 12:
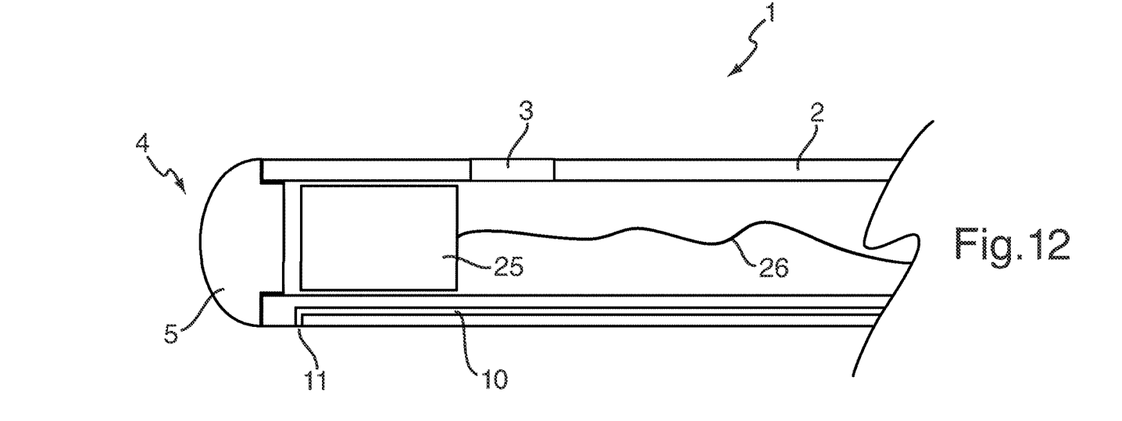
Figure 13:
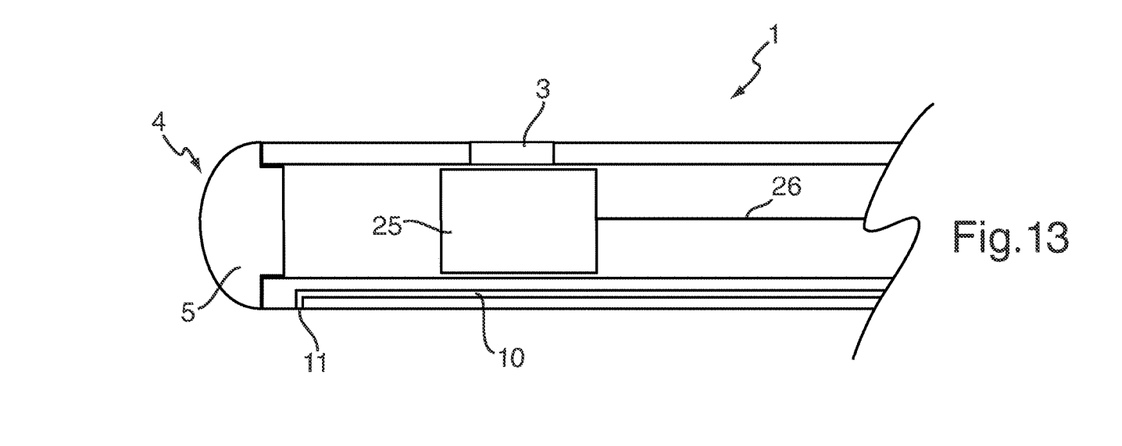

FIGS. 12 and 13 illustrate the distal end of an alternative embodiment of a catheter of the present invention, generally indicated by 1. In this embodiment, there is provided a drainage tube 2 again having a drainage opening 3 in its side wall. The drainage tube 2 is again sealed at its distal end 4 by means of a cap 5. In this embodiment, the closure member is in the form of a plug 25 located within the lumen of the drainage tube 2 and so shaped and sized as to provide a slidable but generally fluid-tight seal between the outside surface of the plug 25 and the inner surface of the drainage tube 2. The plug 25 is connected to a filament 26 that extends to a proximal end of the catheter and exiting the drainage tube 2 either at its end or, more preferably, through a side wall of the drainage tube 2. In use, when it is required to seal the drainage outlet 3, tension may be applied to the filament 26 to bring the plug 25 across the face of the drainage outlet 3 (or even further down the drainage tube) thereby sealing the flow path. The use of a filament, such as a length of nylon thread, renders the closure mechanism effectively irreversible due to the fact that the filament 26 is capable of transmitting forces in tension, but not in compression.

In any embodiment described herein, it is particularly preferred that a fluid such as a light silicone grease be applied between the interior face of the drainage tube and the outer face of the closure member, either when the closure member is a plug 25 or a secondary tube 7. The use of such a fluid serves two purposes: firstly to lubricate the relative sliding movement of the closure member and the drainage tube and, secondly to provide a more water tight seal there between.

In use, the catheter would be initially configured such that there is an open passage between the drainage opening 3 and the drainage outlet port 27. The catheter would be inserted into the body cavity, for example into the urinary bladder via the urethra, until fluid, such as urine, was seen to discharge from the drainage outlet port 27, which could be conveniently connected to a collection bag via, e.g. a catheter tip connector. Once fluid was seen to discharge from the port, this would indicate that the catheter was in a suitable position within e.g. the bladder and, if one were provided, the location balloon 23 could be inflated to secure the catheter in place. It is particularly preferred and envisaged, however, that no such balloon 23 is provided, but that the proximal end of the catheter could merely be taped in to position on an extremity of a patient, for example on the patient's leg to secure the catheter in place whilst the drainage and/or instillation of a drug were carried out. To aid such securement, a clip member may be provided into which the proximal end of the catheter can be secured and the clip fastened to the patient either with adhesive tape or some other releasable means.

Once sufficient fluid (e.g. urine) had been drained from the body cavity, the closure member may be actuated to close the flow path between the drainage opening and the drainage outlet. At this stage, if medicament is to be administered, it can be introduced into the body cavity by injection through the instillation port 17 at the proximal end of the catheter, to emerge at the instillation outlet 11 via the instillation lumen 10.

Figure 14A:
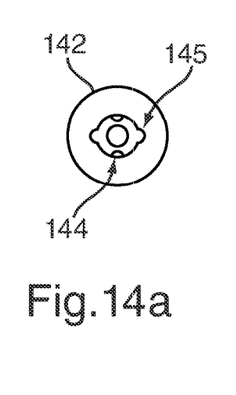
FIGS. 14-16 illustrate a delivery means for a medicament suitable for use with a catheter in accordance with the invention.
Figure 14B:
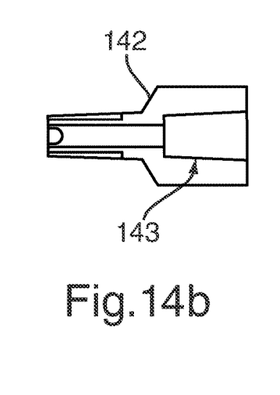
Figures 15A, 15B:
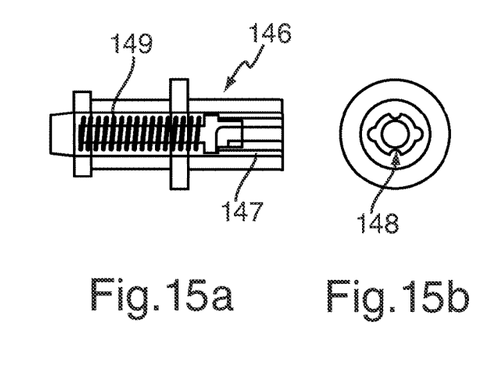
Figure 16:
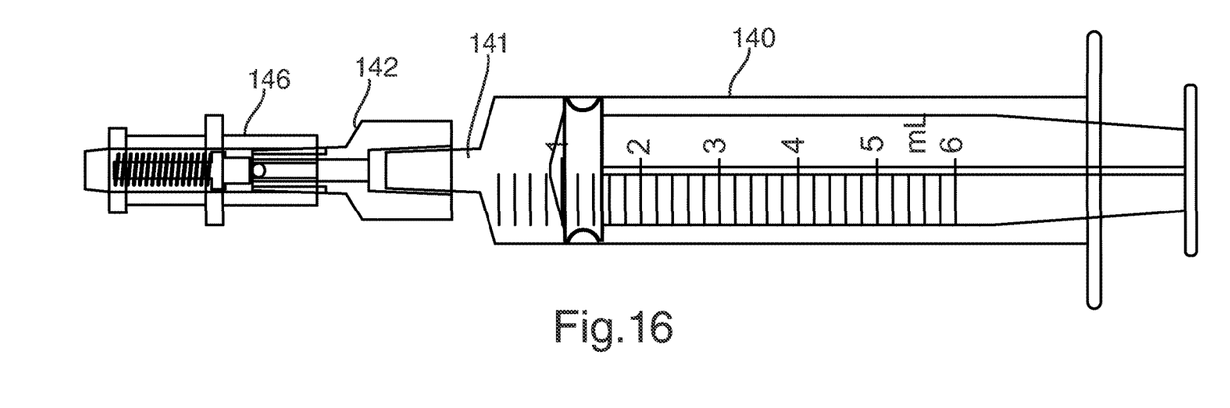

An example of a syringe and connector suitable for the administration of a medicament is illustrated in FIGS. 14-16. A standard syringe 140 is utilized to retain and deliver a measured volume through the syringe outlet 141. The syringe outlet 141 is housed in, and connected to, the instillation port 17 (FIG. 10), by an adapted Luer slip connector. The adaptations described below prevent the connector from being used in conjunction with standard Luer fixtures.

The connector comprises two main elements. The first element is an adapter 142 having, at a first end, a tapered recess 143 to receive the syringe outlet 141. The outlet 141 and recess 143 connect via a push fit connection although additional bonding means can be included to provide a more secure connection. The second end of the adapter 142, shown in the end view FIG. 15a has recessed channels 144 and raised ribs 145, which achieve the prevention of the fitment of the adapter 142 to a standard Luer as mentioned above.

The adaptor 142 itself is seated in a one-way valve fitting 146 having at a first end a recess 147 of shape complementary to that of the channels 144 and ribs 145 to provide a secure fitting. The raised ribs 148 within the recess 147 prevent a standard Luer fitting from being inserted. The second end of the valve fitting 146 can be fitted to the instillation port 17. The one-way valve fitting 146 includes a spring 149 or other resilient means known in the art to bias the valve 146 to the closed position when no pressure is exerted on the fluid in the syringe 140. The assembled syringe and connector, including the adapter 142 and valve fitting 146 is shown in FIG. 16.

Once administration is complete, the locational balloon 23 (if present) may be deflated, and the catheter withdrawn from the body cavity for disposal.

The invention claimed is:

1. A urinary catheter for insertion into a urinary bladder of a subject, comprising:
    a drainage tube extending from a drainage opening adjacent a distal end of the catheter to a drainage outlet adjacent a proximal end of the catheter, wherein the proximal end of the catheter is configured for positioning outside the subject with the distal end of the catheter within the subject;
    a closure member located adjacent the distal end of the catheter and movable within said drainage tube between an open position and a closed position:
        in the open position said drainage opening is aligned with an aperture of the closure member, and
        in the closed position the drainage opening is misaligned with the aperture of the closure member and the drainage tube is closed adjacent to the distal end of the catheter;
    an actuator coupled with the closure member and operable from the proximal end of the catheter, the actuator configured to remotely move said closure member adjacent the distal end between said open and closed positions; and
    an instillation lumen extending from an instillation port adjacent the proximal end of the catheter to an instillation outlet adjacent the distal end of the catheter, the instillation outlet is configured to discharge into the urinary bladder, wherein the instillation lumen is isolated from the drainage tube and the closure member.

2. The catheter according to claim 1 further comprising a non-return valve configured to resist flow in said instillation lumen in a direction from a distal end to a proximal end.

3. The catheter according to claim 1 wherein said actuator is configured to move said closure member between said open and closed positions irreversibly.

4. The catheter according to claim 1 wherein said closure member comprises a secondary tube located within said drainage tube, said secondary tube having the aperture in its wall, and wherein said secondary tube extends to the proximal end of said catheter such that it may be manipulated to slideably move said secondary tube between the open and closed positions, thereby acting as said actuator.

5. The catheter according to claim 4 configured such that said sliding movement is in an axial direction.

6. The catheter according to claim 5 wherein a cross-sectional profile of said drainage tube and a profile of an outside surface of said secondary tube are so shaped as to resist relative rotational movement therebetween while allowing relative axial movement therebetween.

7. The catheter according to claim 4 configured such that said sliding movement comprises rotation of said secondary tube relative to said drainage tube.

8. The catheter according to claim 7 wherein a cooperating indent and detent provided on an outside surface of said secondary tube and an internal wall of said drainage tube, respectively, are configured to allow relative rotational movement between the secondary tube and the drainage tube while resisting relative axial movement therebetween.

9. The catheter according to claim 7 further comprising a lubricating agent provided between the closure member and an internal wall of the drainage tube to provide a fluid resistant seal.

10. The catheter according to claim 1 further comprising a lubricating agent provided between said closure member and an internal wall of said drainage tube to facilitate relative movement.

11. The catheter according to claim 1 wherein a ratchet mechanism is provided to ensure irreversible movement of the closure member relative to the drainage tube.

12. The catheter according to claim 1 further comprising a balloon adjacent an external wall of the catheter near the catheter distal end and proximal of said drainage opening and connected through a balloon control channel to a balloon control port at the proximal end of the catheter, the balloon being inflatable and deflatable to respectively increase and decrease the local diameter of the catheter to allow reversible anchoring of the catheter within the subject.

13. The catheter according to claim 1 further comprising a lubricating agent provided between the closure member and an internal wall of the drainage tube to provide a fluid resistant seal.

14. The catheter of claim 1 wherein the closure member is located adjacent the drainage opening.

15. A method of instilling a medicament into a urinary bladder of a human or animal subject, the method comprising:
    providing a catheter according to claim 1 configured such that the drainage tube extends from the drainage opening to the drainage outlet port;
    inserting the catheter into the urinary bladder via a urethra;
    draining urine from the urinary bladder through the drainage tube;
    actuating the closure member to close the drainage tube between the drainage opening and the drainage outlet and adjacent the distal end of the catheter;
    introducing a medicament into the urinary bladder through the instillation lumen and outlet.

16. The method of claim 15 wherein the subject is a human.

17. The method of claim 15, wherein introducing the medicament into the urinary bladder is after actuating the closure member to close the drainage tube.

18. A urinary catheter for insertion into a urinary bladder of a subject, comprising:
    a drainage tube extending from a drainage opening adjacent a distal end of the catheter to a drainage outlet adjacent a proximal end of the catheter, wherein the proximal end of the catheter is configured for positioning outside the subject while the distal end is within the subject;
    a closure member movable within the drainage tube between open and closed positions, wherein the closure member includes a secondary tube within the drainage tube:
        in the open position an aperture of the secondary tube is aligned with the drainage opening at the distal end, and
        in the closed position the secondary tube is moved relative to the drainage tube, and the aperture is misaligned with the drainage opening;
    wherein the secondary tube is operable from the proximal end of the catheter and configured to move the aperture relative to the drainage opening adjacent the distal end of the catheter; and
    an instillation lumen extending from an instillation port adjacent the proximal end of the catheter to an instillation outlet adjacent the distal end of the catheter, the instillation outlet is configured to discharge into the urinary bladder, wherein the instillation lumen is isolated from the drainage tube and the closure member.

19. The catheter according to claim 18 wherein when the closure member is in the closed position the drainage opening is not in fluid communication with the drainage tube.

* * * * *

UNITED STATES PATENT AND TRADEMARK OFFICE
CERTIFICATE OF CORRECTION

PATENT NO. : 10,188,827 B2  
APPLICATION NO. : 14/351936  
DATED : January 29, 2019  
INVENTOR(S) : Glickman et al.

Page 1 of 1

It is certified that error appears in the above-identified patent and that said Letters Patent is hereby corrected as shown below:

On the Title Page

Item (72), in "Inventors", in Column 1, Line 1, after "Aylesbury", insert --, Buckinghamshire--

Item (72), in "Inventors", in Column 1, Line 2, after "Bungay", insert --, Suffolk--

Signed and Sealed this
Fifteenth Day of December, 2020

Andrei Iancu
*Director of the United States Patent and Trademark Office*